United States Patent [19]

Niklas et al.

[11] 4,070,917

[45] * Jan. 31, 1978

[54] ULTRASONIC PULSE-ECHO THICKNESS AND VELOCITY MEASURING METHOD

[75] Inventors: Ludwig Niklas, Lovenich, Germany; Philip A. Walker, Trumbull, Conn.

[73] Assignee: Krautkramer-Branson, Incorporated, Stratford, Conn.

[*] Notice: The portion of the term of this patent subsequent to Nov. 30, 1993, has been disclaimed.

[21] Appl. No.: 687,896

[22] Filed: May 19, 1976

Related U.S. Application Data

[62] Division of Ser. No. 618,074, Sept. 30, 1975, Pat. No. 3,994,154.

[51] Int. Cl.² .............................................. G01N 29/00
[52] U.S. Cl. ........................................................ 73/598
[58] Field of Search .................. 73/67.8 R, 67.7, 67.6, 73/67.5 R, 67.9

[56] References Cited

U.S. PATENT DOCUMENTS

| | | | |
|---|---|---|---|
| 2,612,772 | 10/1952 | McConnell | 73/67.8 R |
| 3,605,504 | 9/1971 | Kummer et al. | 73/67.7 |
| 3,994,154 | 11/1976 | Niklas et al. | 73/67.8 R |

FOREIGN PATENT DOCUMENTS

| | | | |
|---|---|---|---|
| 1,162,428 | 8/1969 | United Kingdom | 73/67.8 R |

*Primary Examiner*—Anthony V. Ciarlante
*Attorney, Agent, or Firm*—Ervin B. Steinberg; Philip J. Feig

[57] ABSTRACT

In a pulse-echo ultrasonic circuit an ultrasonic search signal is periodically transmitted into a workpiece. The ensuing pair of echo signals (entrant and rear surface reflection respectively) are fed to a timing circuit for providing a timing signal responsive to the time interval between the two echo signals. A fixed pulse width pulse generator is triggered responsive to the search signal. The output from the fixed pulse width generator and the timing signal from the timing circuit are selectively fed to a converter circuit for providing an output signal indicative of workpiece thickness or workpiece acoustic velocity. The converter circuit includes adjustable parameters comprising current magnitude and resistance to provide suitable calibration. Similar calibration is achieved also by varying the repetition rate of the search signal.

9 Claims, 4 Drawing Figures

ULTRASONIC PULSE-ECHO THICKNESS AND VELOCITY MEASURING METHOD

This is a division, of application Ser. No. 618,074, filed Sept. 30, 1975 now U.S. Pat. No. 3,994,154.

BRIEF SUMMARY OF THE INVENTION

The present invention concerns an electrical circuit for a pulse-echo ultrasonic thickness and velocity measuring apparatus. Specifically, the circuit includes means for providing pulses commensurate with a predetermined time interval for measuring the acoustic velocity of a workpiece having a known thickness or alternatively for measuring the thickness of a workpiece having a known acoustic velocity.

In prior pulse-echo ultrasonic measuring apparatus complex and expensive circuits are required for obtaining both workpiece thickness and acoustic velocity measurements. In certain prior apparatus, such as time averaging circuits, a plurality of clocks, digital counters and storage means are used to perform the thickness and acoustic velocity measurements. In other devices, an operator must calibrate the apparatus while observing a cathode ray tube. The present invention in a preferred example makes use of a fixed pulse width pulse generator and a switch in combination with conventional electrical circuits to provide a less expensive and simpler pulse-echo ultrasonic thickness and velocity measuring apparatus.

In the present invention, as in other ultrasonic apparatus, a transmit-receive transducer probe, suitably coupled to a workpiece, is caused to periodically transmit ultrasonic search signals into the workpiece and to receive acoustic discontinuity responsive echo signals therefrom. A receiver circuit electrically connected to the transducer probe receives the entrant surface and rear wall echo responsive electrical signals and provides video pulses commensurate with the receipt of the two mentioned signals.

The video pulses are conducted to a timing system, the construction of which is well known in the art, for generating a timing signal having a pulse width equal to the time interval between the receipt of the entrant surface and rear wall responsive echoes. The timing signal, in a preferred embodiment, is then provided to a time to analog converter circuit which circuit provides an output analog voltage signal commensurate with the duty cycle of the timing signal. To measure the acoustic velocity of a workpiece having a known thickness, the time to analog converter circuit is adjusted until the output analog voltage signal from the converter circuit is commensurate with the known workpiece thickness. Upon substituting pulse signals having a predetermined pulse width and repetition rate for the timing signals at the input of the converter circuit, the output analog voltage signal of the time to analog converter circuit is responsive to the acoustic velocity of the workpiece.

In an alternative embodiment, the timing signal is provided to a digital converter circuit which circuit provides an output digital signal commensurate with the pulse width of the timing signal. A clock input signal to the digital converter circuit is adjusted to provide an output digital signal commensurate with the known workpiece thickness. When fixed pulse width pulses are substituted at the input of the digital converter circuit for the timing signal, the output digital signal is indicative of the acoustic velocity of the workpiece.

A principal object of the present invention, therefore, is the provision of an electrical circuit for use in a pulse echo ultrasonic measuring apparatus which provides a signal indicative of the acoustic velocity of a workpiece having a known thickness.

Another object of the present invention is the provision of an electrical circuit for use in a pulse-echo ultrasonic measuring apparatus which provides a signal indicative of the thickness of a workpiece having a known acoustic velocity.

A further object of the present invention is the provision of an electrical circuit including fixed pulse width generating means for use in a pulse-echo ultrasonic thickness/acoustic velocity measuring apparatus.

Further and still other objects of the present invention will become more clearly apparent when the specification is read in conjunction with the accompanying drawings.

DETAILED DESCRIPTION OF THE INVENTION

Figure 1:
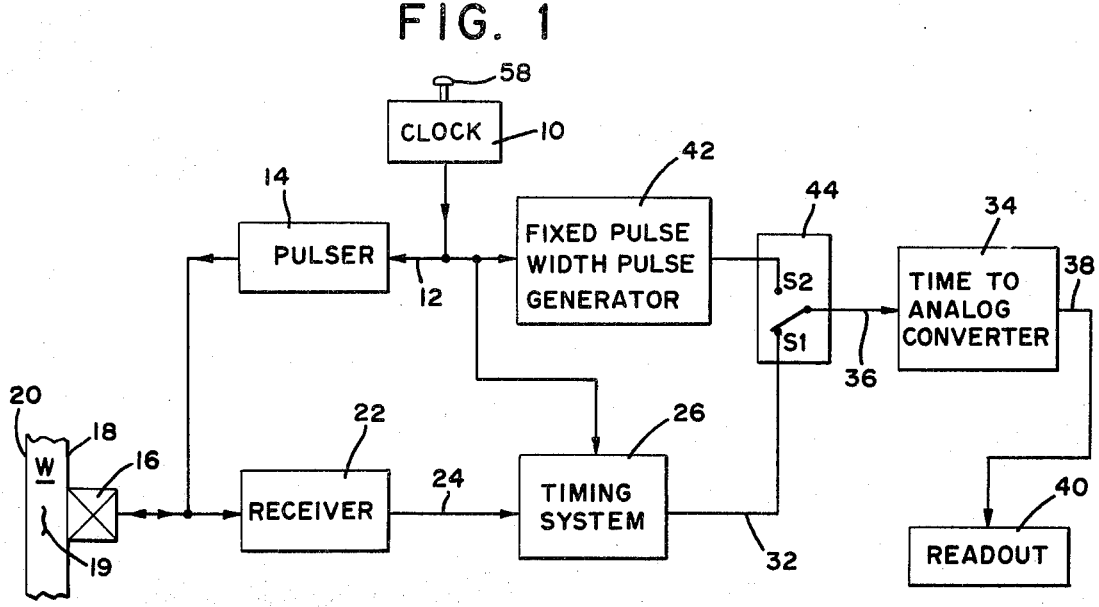
FIG. 1 is a schematic electrical block circuit diagram of a preferred embodiment of the invention.

Referring to the figures and FIG. 1 in particular, there is shown a schematic electrical block circuit diagram of the present invention. A clock 10 provides timing pulses along conductor 12, typically at a frequency in the range between 50 Hz and 20 kHz, to a pulser circuit 14. The pulser circuit 14, responsive to the receipt of a timing pulse, provides a signal for periodically energizing a transmit-receive transducer probe 16 acoustically coupled to a workpiece W via water, oil, or other suitable couplant, for transmitting ultrasonic energy search signals into the workpiece W. A portion of the transmitted energy upon intercepting an acoustic discontinuity, such as the entrant surface 18 of the workpiece W, is reflected back toward the probe 16. The search signal continues traveling at a velocity equal to the acoustic velocity of the workpiece through the thickness of the workpiece W until intercepting the rear wall 20 whereat a second portion of the search signal is reflected back through the workpiece W and couplant to the probe 16.

Figure 2:
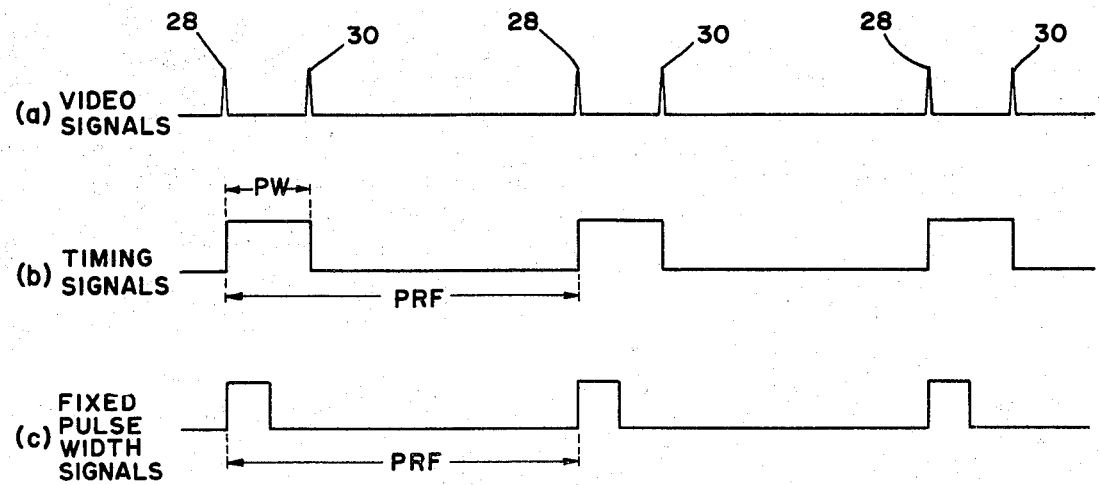
FIG. 2 is a graphical representation of electrical signals generated within the circuit per FIG. 1.

The two mentioned reflected echo signals are converted into echo responsive electrical signals by the probe 16, which electrical signals are provided to a receiver circuit 22. The receiver circuit 22, in turn, provides via conductor 24 to the timing system 26, comprising a flip flop, a pair of echo responsive video signals, shown schematically in FIG. 2, trace *a*, as pulses 28 and 30, commensurate with the search signal intercepting the entrant surface 18 and the rear wall 20 of the workpiece W respectively. The timing system 26, in turn, provides along conductor 32 to contact S1 of switch 44 a timing signal having a pulse width PW. The timing system 26 is reset by a signal received from the clock 10 prior to the transmission of a respective search signal. As seen in FIG. 2, trace *b*, the timing signal pulse commences responsive to the receipt by the timing system 26 of the entrant surface echo responsive video signal 28 and terminates responsive to the receipt of the rear wall echo responsive video signal 30. The pulse width PW therefore has a duration corresponding to the time required for the ultrasonic search signal traveling at the acoustic velocity of the workpiece to traverse twice the thickness of the workpiece W so that:

$$PW = \frac{2 \times \text{thickness of the workpiece}}{\text{acoustic velocity of the workpiece}} \qquad \text{eq. 1}$$

A pulse generating means, such as a fixed pulse width generator 42 triggered concurrently with the pulser 14 provides at switch 44 contact S2 pulses signifying a predetermined time interval or pulse width at the repetition frequency determined by the frequency of clock 10 as shown in FIG. 2, trace c.

Figure 3:
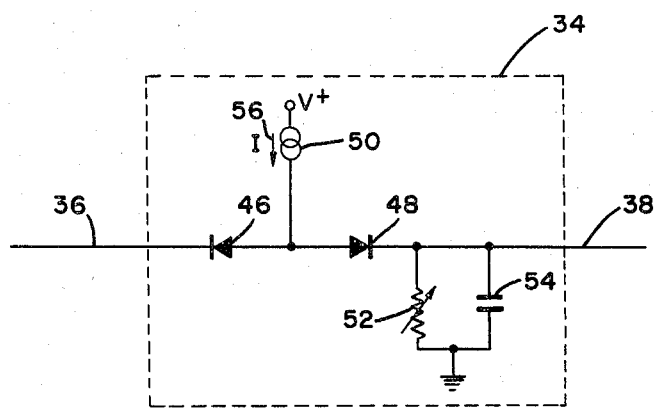
FIG. 3 is a schematic electrical circuit diagram of a portion of the circuit per FIG. 1.

The time to analog converter circuit 34, shown in detail in FIG. 3, receives along conductor 36 either timing signals from timing system 26 or fixed pulse width signals from generator 42 via the switch 44 and provides at its output 38 an analog voltage signal commensurate with the duty cycle of the input signal.

Readout means 40, such as a display, recorder, or the like, receives the analog voltage signal and provides an indication of the workpiece characteristic being measured. The readout means 40 also includes scaling means for converting the analog voltage to units of velocity or thickness as well as means for converting the measured values from metric to English units and vice versa.

CIRCUIT OPERATION

The description provided hereinafter is most applicable for measuring the acoustic velocity of a workpiece having a known thickness. It will become apparent to those skilled in the art that the converse operation can be performed for measuring the thickness of a workpiece having a known acoustic velocity.

The switch 44 is initially placed in the position for coupling the timing signal from timing system 26 via conductor 32, switch contact S1 and conductor 36 to the time to analog converter circuit 34. The timing signal is coupled to the cathode of a diode 46 as shown in FIG. 3. The anode of diode 46 is coupled to the junction of the anode of diode 48 and constant current generator 50. The cathode of diode 48 is connected to a first end of the parallel combination of a variable resistor 52 and capacitor 54 as well as to output 38. The other end of the parallel combination is connected to ground potential.

Diode 46 is rendered conductive for conducting current from current generator 50 to timing system 26 via switch 44 when the timing signal along conductor 36, shown in FIG. 2, trace b, is in its low condition and is rendered non-conductive when the timing signal is in its high condition. Current generator 50 provides a constant current I in the direction of arrow 56. The current I flows through diode 46 when the diode 46 is rendered conductive and flows through diode 48 and resistor 52 to ground when diode 46 is rendered non-conductive. The average current $I_o$ flowing through diode 48 and hence through resistor 52 is equal to:

$$I_o = PW \times I \times PRF \qquad \text{eq. 2}$$

where PRF is the pulse repetition frequency of the pulse-echo ultrasonic measuring apparatus in units of pulses per second.

The analog voltage (V) appearing at output 38 of the time to analog converter circuit 34 is the product of the average current $I_o$ times the resistance (R) of resistor 52, that is $$V = PW \times I \times PRF \times R \qquad \text{eq. 3}$$

The pulse width (PW) is fixed for a workpiece of known thickness and acoustic velocity. Hence, to cause the output analog voltage (V) to be of a value such that readout means 40 displays a value commensurate with the workpiece thickness either the constant current (I) from current generator 50, or the resistance (R) of variable resistor 52 or the pulse repetition frequency (PRF) of the apparatus must be adjusted.

In a preferred embodiment, the current I from current generator 50 is adjusted for providing coarse adjustment and the resistance R of variable resistor 52 is adjusted for providing fine adjustment during calibration of the measuring apparatus. It will be apparent that either one of the stated parameters alone can be adjusted. For simplicity, in the following description it is assumed that only the resistance R of variable resistor 52 is varied.

The readout means 40 displays a value commensurate with the analog voltage V. When the displayed value is equal to the known workpiece thickness the following relationship exists:

$$\text{thickness} = PW \times I \times R' \times PRF \qquad \text{eq. 4}$$

wherein R' is the adjusted resistance value of the variable resistor 52 for providing the display commensurate with the known workpiece thickness. By substituting equation 1 into equation 4, $$\text{thickness} = \frac{2 \times \text{thickness} \times I \times R' \times PRF}{\text{acoustic velocity}} \qquad \text{eq. 5}$$

by mathematical manipulation equation 5 reduces to:

$$R' = \frac{\text{acoustic velocity}}{2 \times I \times PRF} \qquad \text{eq. 6}$$

After the variable resistor 52 is adjusted to the resistance value R', the switch 44 is changed to the position for coupling the fixed pulse width signal at contact S2 to the time to analog converter circuit 34 via conductor 36. The fixed pulse width signal in a preferred embodiment is twenty microseconds in duration and occurs at a typical pulse repetition frequency of 1 kilohertz.

The analog voltage V at the output 38 of the time to analog converter 34 is thus:

$$V = 20 \times I \times PRF \times R' \qquad \text{eq. 7}$$

and substitution of equation 6 into equation 7 yields $$V = 20 \times I \times PRF \times \frac{\text{acoustic velocity}}{2 \times I \times PRF} \qquad \text{eq. 8}$$

or $$V = 10 \times \text{acoustic velocity}$$

The readout means 40 is designed for automatically performing decade division for displaying the analog voltage responsive signal directly in units of velocity. While a pulse width of twenty microseconds is used in the foregoing description, any fixed pulse width pulse can be provided by generator 42 provided that the readout means 40 or the apparatus in general includes means for providing proper scaling.

To measure the thickness of thin workpieces, the frequency of the timing pulses from clock 10 and hence, the pulse repetition frequency of the timing signals is increased to approximately ten kilohertz. The current I from current generator 50 and the resistance R of variable resistor 52 are adjusted as described above for causing the readout means 40 to display a value commensurate with the workpiece thickness when the switch 44 is in position S1. Since the pulse repetition frequency (PRF) in equation 3 has been increased by a factor of ten, the pulse width (PW) must be decreased by a factor of ten when fixed pulse width pulses at the higher repetition frequency are provided to contact S2 of switch 44. To obviate the requirement of generating a pulse signal having a 2 microsecond pulse width and a 10 kilohertz repetition rate, the original fixed pulse width signal is provided to contact S2 of switch 44. That is, a 20 microsecond pulse having a repetition rate of 1 kilohertz is provided to switch contact S2 even though the apparatus repetition rate has been increased to ten kilohertz.

In an alternative embodiment, the clock 10 includes a knob 58 for adjusting the pulse repetition rate of the timing pulses. By varying the pulse repetition rate of the measuring apparatus the duty cycle of timing signals per FIG. 2, trace b, and hence, the duty cycle of the fixed pulse width signals per FIG. 2, trace c, is varied. If the current I from current generator 50 and the resistance R of variable resistor 52 are left unchanged, the read-out means 40 can be made to display a value commensurate with the known thickness of a workpiece when the switch is in position S1 by turning knob 58, thereby changing the pulse repetition frequency PRF of the measuring apparatus. In a like manner, the readout means 40 can be made to display a value commensurate with the known acoustic velocity of the workpiece when the switch 44 is in position S2.

In the above description the current I from current generator 50 and resistance R of variable resistor 52 are adjusted in the preferred embodiment and the pulse repetition rate (PRF) is adjusted in an alternative embodiment of the invention. It will be apparent that the variable parameters (I, R, or PRF) can be varied either singly or in combination to achieve the desired objective of the present invention, namely, the provision of an ultrasonic pulse-echo measuring apparatus for measuring thickness or acoustic velocity of a workpiece.

While the foregoing description concerns the measurement of the acoustic velocity of a workpiece having a known thickness, it will be apparent that by initially causing switch 44 to be in position S2 while adjusting the variable parameters (I, R, or PRF) for causing readout means 40 to display a value equal to the known acoustic velocity of a workpiece, the thickness of the workpiece is displayed when the switch is moved to position S1.

In a further variation, the parameters of the apparatus are adjusted when switch 44 is in position S2 until the readout means displays the indicia 1.000. The switch is then moved to position S1 and the readout means now displays the transit time of an ultrasonic search signal traveling through the workpiece in units of microseconds.

Figure 4:
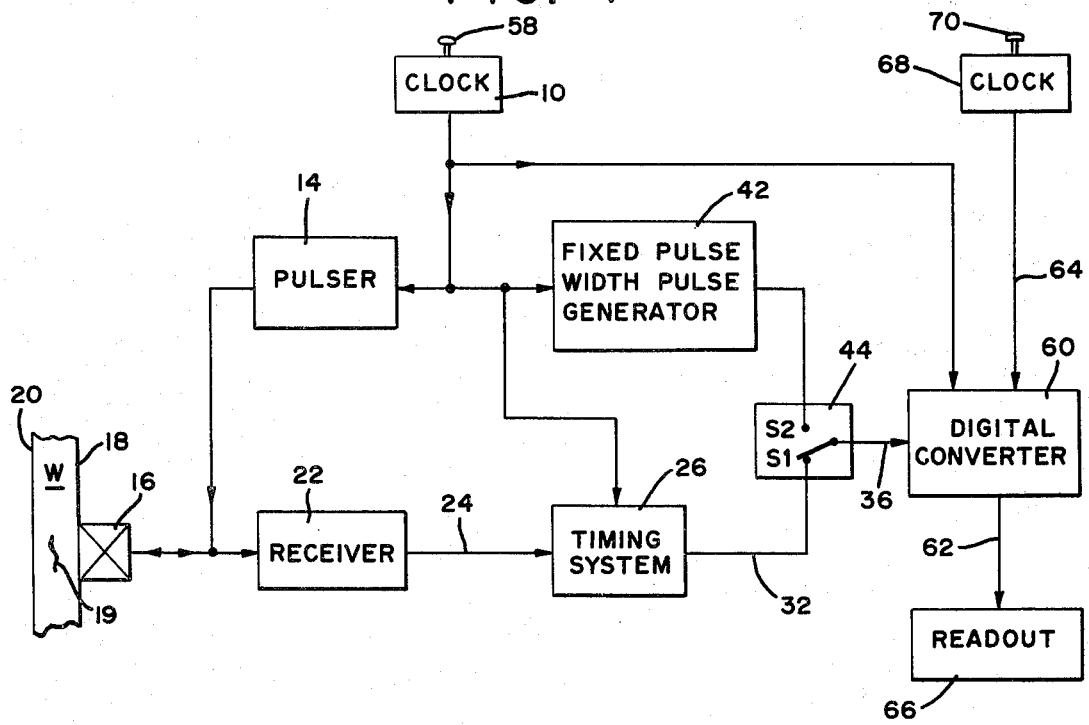
FIG. 4 is a schematic electrical circuit diagram of an alternative embodiment of the invention.

In FIG. 4 an alternative embodiment of the circuit is shown wherein the time to analog converter 34 is replaced by a digital converter circuit 60. The digital converter circuit 60 preferably is a gated counter, that is, the output digital signal along conductor 62 is commensurate with the quantity of clock pulses received from a high frequency clock 68 along conductor 64 during the time interval determined by the timing signal (FIG. 2, trace b) provided along conductor 32, switch 44 and conductor 36.

To measure the acoustic velocity of a workpiece W having a known thickness, a timing pulse from clock 10 resets digital converter circuit 60. The timing signals, FIG. 2, trace b, are transmitted from timing system 26 via conductor 32, switch 44 and conductor 36 to digital converter circuit 60. The frequency of the clock pulses transmitted along conductor 64 is adjusted by turning knob 70 until the output signal along conductor 62 is commensurate with the known workpiece thickness as evidenced by the value displayed by readout means 66. When switch 44 is changed to position S2, fixed pulse width pulses, FIG. 2, trace c, are substituted at the input of the digital converter circuit 60. The output digital signal along conductor 62 is commensurate with the acoustic velocity of the workpiece W and readout means 66 displays a value indicative of the acoustic velocity of the workpiece.

Readout means 66 includes decoding means for converting the output digital signal along conductor 62 into a signal compatible with the display device.

In the above example, one specific embodiment of the digital converter circuit 60 has been described. It will be apparent, however, that other pulse width to digital converter circuits, including time averaging circuits, may be substituted for the digital converter 60. Also as shown, the timing signal is generated responsive to the receipt of the entrant surface responsive echo signal. It is possible of course, to initiate the timing signal by electrically providing a signal to the timing system coincident with the timing pulse and then to delay the signal by a time interval sufficient for the ultrasonic search signal to travel from the probe 16 through the couplant or delay means until it reaches the entrant surface 18 of the workpiece W. The timing signal is still terminated responsive to the receipt of the rear wall responsive echo signal.

The pulse-echo thickness measuring apparatus can also be used to measure the distance from the entrant surface 18 of a workpiece W to an acoustic discontinuity 19. In such a case, the video signal 30 will be responsive to the receipt of an echo signal reflected from the discontinuity 19. While the probe is transmitting ultrasonic search signals into a defect free portion of the workpiece the switch 44 is placed in position S2 and the readout means is caused to display the known acoustic velocity of the workpiece W. Upon the switch 44 subsequently being placed in position S1 and the ultrasonic search signal intercepting a defect 19, the readout means will display the distance between the entrant surface 18 and the acoustic discontinuity 19.

While in the above description a preferred embodiment and several modifications of the present pulse-echo ultrasonic measurement apparatus have been described, it will be apparent to those skilled in the art that further variations and modification can be made without deviating from the broad principle of the present invention which shall be limited solely by the scope of the appended claims.

What is claimed is:

1. The method of measuring characteristics of a workpiece by the pulse-echo ultrasonic technique comprising the steps of:
producing timing pulses from a clock;
providing a pulse signal commensurate with a predetermined time interval;
periodically transmitting an ultrasonic search signal into the workpiece responsive to said timing pulses and receiving a corresponding echo signal arising from the search signal intercepting an acoustic discontinuity in the workpiece;
providing a timing signal commensurate with the time interval between said search signal entering the workpiece and the receipt of said echo signal;
coupling said pulse signal and said timing signal sequentially to a converting means, and
providing respective output signals from said converting means responsive to said sequentially coupled signals, said output signals being commensurate with workpiece characteristics.

2. The method as set forth in claim 1, said output signals being commensurate respectively with the acoustic velocity and the thickness of the workpiece.

3. The method as set forth in claim 1, said converting means producing a time analog output signal.

4. The method as set forth in claim 1, said converting means receiving additional clock pulses and producing a digitized output signal.

5. The method as set forth in claim 1, said timing signal and said pulse signal having the same pulse repetition frequency.

6. The method as set forth in claim 1, said timing signal and said pulse signal having different pulse repetition frequencies.

7. The method as set forth in claim 1 and displaying a value indicative of said respective output signals.

8. The method as set forth in claim 1, said pulse signal having a predetermined pulse width.

9. The method as set forth in claim 1, providing said pulse signal responsive to said timing pulses.

* * * * *